United States Patent
Zhang et al.

(10) Patent No.: US 10,976,247 B2
(45) Date of Patent: Apr. 13, 2021

(54) NIR SPECTROSCOPY METHOD FOR FATTY ACID CONTENT OF OILSEEDS

(71) Applicant: OIL CROPS RESEARCH INSTITUTE, CHINESE ACADEMY OF AGRICULTURAL SCIENCES, Hubei (CN)

(72) Inventors: Liangxiao Zhang, Hubei (CN); Peiwu Li, Hubei (CN); Zhe Yuan, Hubei (CN); Du Wang, Hubei (CN); Xuefang Wang, Hubei (CN); Wen Zhang, Hubei (CN); Qi Zhang, Hubei (CN)

(73) Assignee: OIL CROPS RESEARCH INSTITUTE, CHINESE ACADEMY OF ARGICULTURAL SCIENCES, Hubei (CN)

( * ) Notice: Subject to any disclaimer, the term of this patent is extended or adjusted under 35 U.S.C. 154(b) by 8 days.

(21) Appl. No.: 16/535,330

(22) Filed: Aug. 8, 2019

(65) Prior Publication Data
US 2020/0049623 A1    Feb. 13, 2020

(30) Foreign Application Priority Data
Aug. 13, 2018   (CN) .......................... 201810917861.4

(51) Int. Cl.
G01N 21/359 (2014.01)
A01H 5/10 (2018.01)
G01N 33/03 (2006.01)

(52) U.S. Cl.
CPC ............. *G01N 21/359* (2013.01); *A01H 5/10* (2013.01); *G01N 33/03* (2013.01)

(58) Field of Classification Search
CPC ................. G01N 21/359; G01N 33/03; G01N 2201/129; G01N 21/3577; A01H 5/10
See application file for complete search history.

(56) References Cited

U.S. PATENT DOCUMENTS

| | | | |
|---|---|---|---|
| 2011/0160594 A1* | 6/2011 | Platsch | G01N 33/5082 600/473 |
| 2014/0323307 A1* | 10/2014 | Ogawa | A01G 7/00 504/320 |

OTHER PUBLICATIONS

Xiabo et al. "Variables selection methods in near-infrared spectroscopy", Analytics Chimica Acta 667 (2010) pp. 14-32 (Year: 2010).*

* cited by examiner

*Primary Examiner* — David P Porta
*Assistant Examiner* — Meenakshi S Sahu
(74) *Attorney, Agent, or Firm* — Tim Tingkang Xia, Esq.; Locke Lord LLP

(57) ABSTRACT

The invention discloses a NIR method for fatty acid content of oilseeds, including: selection of oilseed samples, and analyzing the oilseed samples by an near infrared spectrometer to obtain NIR spectra; preprocessing of NIR spectra and establishment of a NIR spectral database of oilseeds; establishment of a fatty acid database of oilseeds based on gas chromatography; establishment of prediction model of fatty acids in oilseeds; acquiring NIR spectrum of a sample to be tested by the near infrared spectrometer, and importing the preprocessed NIR spectrum into the prediction model of fatty acids to obtain the predicted fatty acid content of the tested sample. The method is simple and rapid to operate and is non-destructive, and the detection time of the sample is greatly shortened and the detection cost is reduced.

4 Claims, 2 Drawing Sheets

NIR SPECTROSCOPY METHOD FOR FATTY ACID CONTENT OF OILSEEDS

CROSS-REFERENCE TO RELATED APPLICATION

This application claims priority to and the benefit of Chinese Patent Application No. 201810917861.4, filed Aug. 13, 2018 in the State Intellectual Property Office of P.R. China, which is hereby incorporated by reference in its entirety.

FIELD OF THE INVENTION

The present invention relates generally to the field of food quality and safety, and more particularly to a NIR spectroscopy method for fatty acid content of oilseeds.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

China is the largest country of food production and consumption. The quality and safety of foods have an important impact on human health. The quality and safety of agricultural products as raw materials are an important and decisive basis. In recent years, the world's attentions to food safety issues have also been increasing, and a great stress has been laid on the quality and safety of agricultural products. After the accession of China to the World Trade Organization (WTO), tariff barriers for China's agricultural products being exported to the world will gradually be replaced by technical barriers, and the functionality and safety of foods are ever more emphasized. On the other hand, the requirements of food manufacturers, government regulators and consumers for food quality analysis methods are shifting toward a real-time, rapid and non-destructive direction. Edible oils are an indispensable part of people's dietary structure. Edible Oils provide energy, essential fatty acids and other nutrients, including fat-soluble vitamins, phytosterols, polyphenols and other functional ingredients for human body, and are also important basic raw materials for the food and feed industries. Quality of edible oils depends on the quality of oilseeds. In this context, new, rapid and efficient detection technology and equipment have become major technological needs in this field.

The traditional detection methods for fatty acid content of oilseeds, such as gas chromatography or gas chromatography-mass spectrometry, require pretreatment of a sample and long detection time. The large amount of chemical reagents used in the detection process will cause certain pollution to the environment, which are not suitable for on-site detection or for nondestructive inspection needs of today's large commodity trading context. For breeders, the amount of sample is limited; for producers, merchants, and regulators, these methods cannot be used for on-site detection, and are not rapid or efficient. Therefore, it is urgent to establish a rapid, non-destructive and environment-friendly detection method for fatty acid content of oilseeds.

Fatty acid content usually refers to relative contents of fatty acids in oilseeds and oilseeds. NIR (NIR) spectroscopy is a rapid, non-destructive and environment-friendly and low-cost measurement and therefore used in quantitative and qualitative analysis of agricultural products and foods. The rapid detection methods currently used need to be combined with chemometric methods to establish a prediction model. Generally, the prediction models are directly constructed by using the relative content of fatty acids in oilseeds and NIR spectra. However, NIR spectrum reflects the information on the absolute content of fatty acids, the absolute contents of fatty acids therefore comply with Lambert Beer's law, but relative contents of fatty acids not. So, such models have poor stability and accuracy and thus cannot be used effectively in practice. The main reason is that the influence of oil content is often neglected. In practice, oil content largely ranges. Taking Chinese rapeseeds as an example, the oil contents are from 30% to 50%.

Therefore, there is an urgent need to develop a rapid detection technique for fatty acids in oilseeds from another perspective.

SUMMARY OF THE INVENTION

One of the objectives of this invention is to provide a method for NIR detection of fatty acid content in oilseeds so as to solve the problems in the prior art.

In one aspect, the invention relates to a method for NIR detection of fatty acid content in oilseeds, including the following steps:

Model construction:

S1, collection of NIR spectrum signals: selecting oilseed samples and analyzing the oilseed samples by a NIR spectrometer to get the NIR spectra;

S2, preprocessing of NIR spectrum and establishment of NIR spectral database for oilseeds: performing standard normal transformation and second derivative data preprocessing on the NIR spectrum data of the collected oilseed samples to obtain preprocessed NIR spectra, and establishing the oilseed NIR spectral database;

S3, establishment of fatty acid database of oilseeds based on gas chromatography: using a gas chromatography analysis method to obtain the relative content of fatty acids in each oilseed sample; using a method for measuring oil content of oilseeds to obtain information on the oil content of each oilseed sample; converting the relative content into absolute content of fatty acids; establishing the fatty acid database of oilseeds composed of the relative content, absolute content and correction coefficient of fatty acids as effective information;

S4, establishment of a prediction model of fatty acids in oilseeds: dividing the oilseed samples into training set and validation set, using a variable selection method in combination with NIR spectra in the training set corresponding to different indicators in fatty acid database of oilseeds to select the corresponding important wavelength, establishing the prediction model of fatty acids in oilseeds by using the selected important wavelength through a chemometric method combined with the absolute content and the correction coefficient of fatty acids; validating the prediction model of fatty acids by the validation set;

Model application:

Taking the sample for testing, collecting the NIR spectrum of the tested sample by a NIR spectrometer, performing preprocessing by the preprocessing method in step S2, and importing the preprocessed NIR spectrum into the prediction model of fatty acids established in step S4 to obtain the predicted fatty acid content of the tested sample.

In one embodiment, the formulae for converting the relative content into the absolute content of fatty acids in step S3 of the present invention are:

$$\overline{M_i} = \sum M_j \cdot y_j,$$
$$Z = \frac{\overline{M_i}}{w_i} - 1$$
$$y_j = x_j \cdot \frac{\overline{M_i}}{w_i}$$

where $y_j$ and $x_j$ represent the relative content (molar percentage of each fatty acid in all of detected fatty acids, mol %) of fatty acids and the absolute content (molar amount of each fatty acid per unit mass of oilseed sample, mol/g) of fatty acids respectively, $M_j$ represents the relative molecular mass of each fatty acid, $\overline{M_i}$ is the weighted average relative molecular mass of the fatty acids in the oilseed, $w_i$ represents the oil content (w/w, %), and z represents the correction coefficient for the mutual conversion of the relative content and the absolute content of fatty acids.

In one embodiment, each oilseed sample is repeatedly measured 3-9 times in step S1 of the present invention.

In one embodiment, the collection conditions of NIR spectra in step S1 of the present invention are listed as below:

The collection temperature of the oilseed sample is 20±5° C., the NIR spectrum measurement range is 4,000-10,000 $cm^{-1}$, the number of scans is 64, and the measurement method is reflection.

In one embodiment, the chemometric method in step S4 of the present invention contains variable selection methods including but not limited to Competitive Adaptive Reweighted Sampling (CARS-PLS), Orthogonal Projection to Latent Structures (OPLS) variable combination population analysis (VCPA) and Iteratively Retain Informative Variables (IRIV), and the modeling method includes partial least squares (PLS), multiple linear regression (MLR) and BP-neural network (BP-NN).

The present invention has, among other things, the following beneficial effects: the present invention adopts CARS-PLS, OPLS, VCPA and other variable selection methods to select the characteristic wavelength of each indicator, and combines PLS, MLR, BP-NN and other modeling methods to establish a rapid prediction model of fatty acids in oilseeds. The oil content of oilseeds is combined to convert the relative content of fatty acids into the absolute content of fatty acids for prediction, and the average relative molecular mass and oil content are used to convert the results into relative content to improve the stability and accuracy of the model, which provides a new direction for the quality rapid measurement technology based on the NIR spectra.

According to the invention, the method is simple to operate and has no special requirements for operators; the method is fast and non-destructive, and is short in sample detection time; the method is environmentally friendly, does not need to use any chemical reagents, and thus, is low in detection cost; and the method can be effectively applied to on-site quality testing of oilseeds, and has broad prospects.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
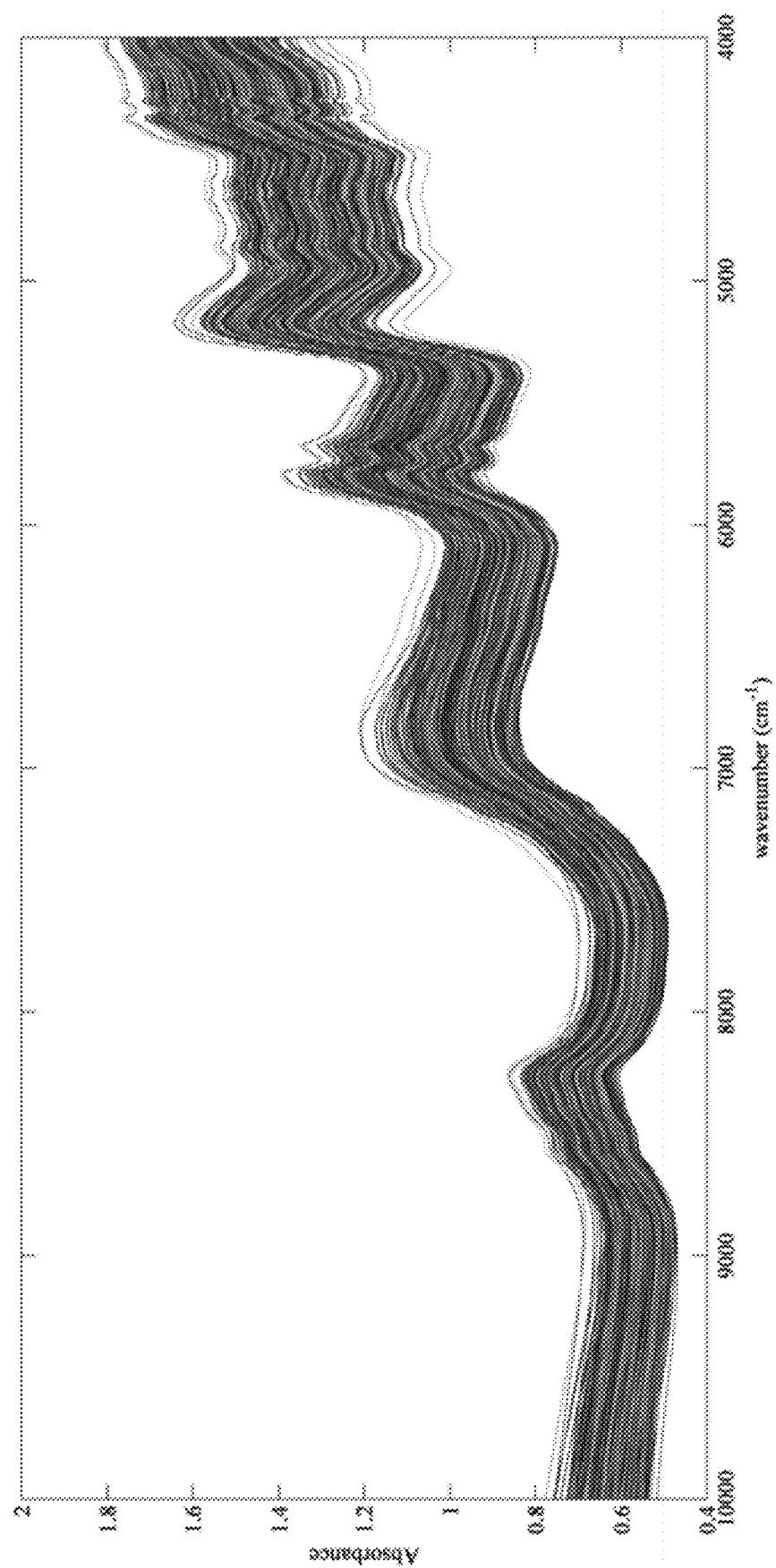
FIG. 1 is an original NIR spectrum of rapeseed according to one embodiment of the present invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In one aspect, the invention relates to NIR method of fatty acid content in oilseeds, including the steps of model construction and model application. The model construction includes the following steps:

S1, collection of NIR spectrum signals: selecting oilseed samples, and analyzing the oilseed samples by a near infrared spectrometer to obtain NIR spectra;

S2, preprocessing of NIR spectra and establishment of NIR spectral database of oilseeds:

performing standard normal transformation and second derivative data preprocessing on the NIR spectra of the collected oilseed samples to obtain preprocessed NIR spectra, and establishing the NIR spectral database of oilseeds;

S3, establishment of fatty acid database of oilseeds based on gas chromatography: using a gas chromatography analysis method to obtain the relative content of fatty acids in each oilseed sample; using a method for measuring oil content of oilseeds to obtain information on the oil content of each oilseed sample; converting the relative content into absolute content of fatty acids; establishing the fatty acid database of oilseeds composed of the relative content, absolute content and correction coefficient of fatty acids as effective information; and S4, establishment of a prediction model of fatty acids in oilseeds: dividing the oilseed samples into training set and validation set, using a variable selection method in combination with NIR spectra in the training set corresponding to different indicators in the fatty acid database of oilseeds to select the important wavelengths, establishing the prediction model of fatty acids in oilseeds by using the selected important wavelengths through a chemometric method combined with the absolute content and the correction coefficient of fatty acids; validating the prediction model of fatty acids by the validation set;

The model application includes taking the sample for testing, collecting the NIR spectra of the tested sample by a NIR spectrometer, performing preprocessing by the preprocessing method in step S2, and importing the preprocessed NIR spectrum into the prediction model of fatty acids established in step S4 to obtain the predicted fatty acid content of the tested sample.

In one exemplary embodiments, the content of linoleic acid in rapeseed sample is taken as an example.

A. Acquisition of sample NIR spectral signals: NIR spectra of 510 rapeseed samples were collected. The spectra acquiring conditions were as follows: the collection temperature was 16±2° C., the NIR spectrum measurement range was 4,000-10,000 cm$^{-1}$, the number of scans was 64, the resolution was 3.857 cm$^{-1}$, and the measurement method was reflection. Each sample was analyzed in triplicate, and the average spectrum was taken as shown in FIG. 1.

Figure 2:
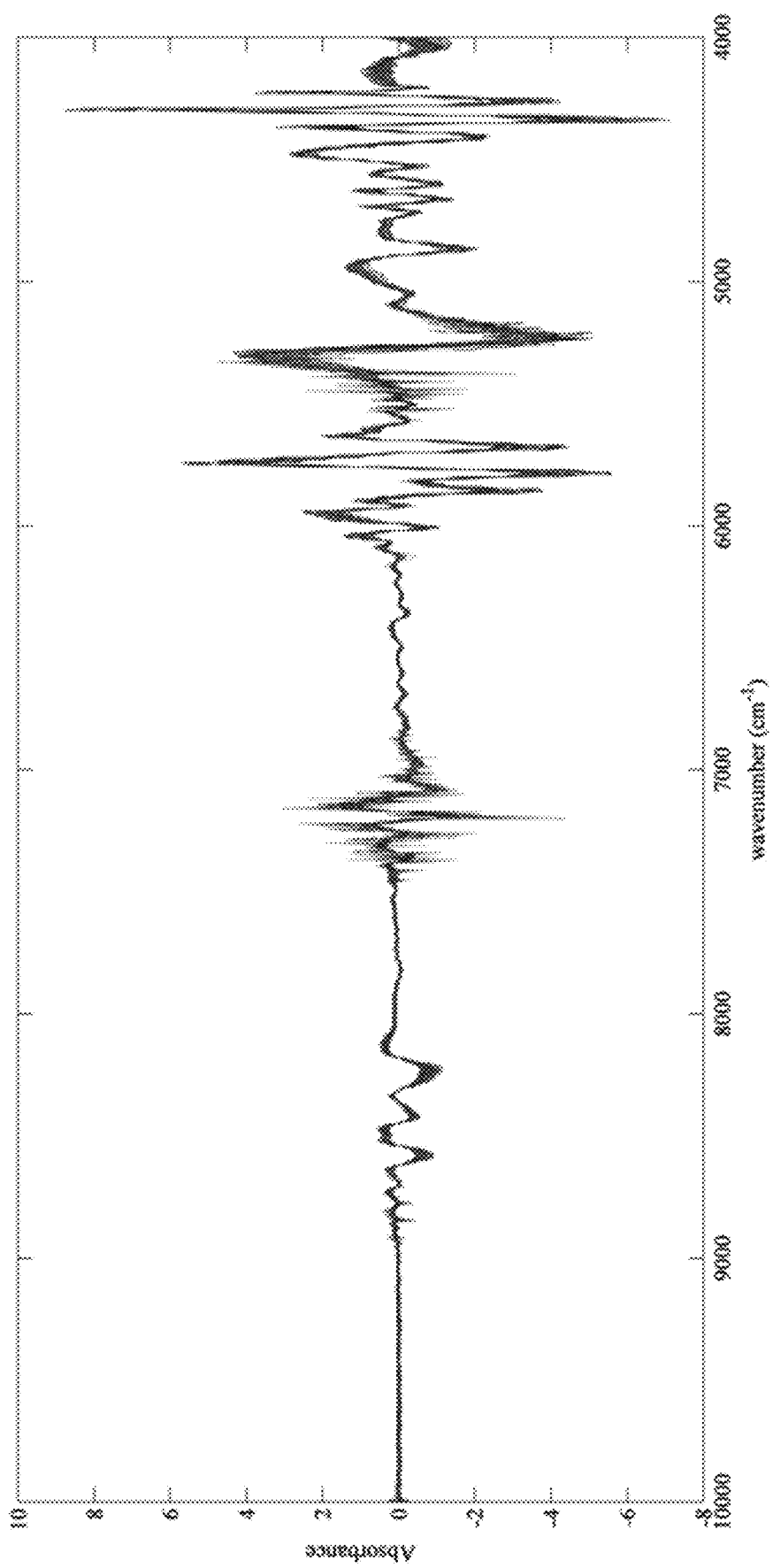
FIG. 2 is a NIR spectrum of the rapeseed after pretreatment according to one embodiment of the present invention.

B. Preprocessing of sample NIR spectra: through experimental research and literature reports, it is found that different preprocessing of spectra before modeling has a great impact on modeling. The method adopts standard normal transformation and second derivative data preprocessing to obtain the preprocessed NIR spectrum of rapeseed as shown in FIG. 2 and to establish a rapeseed NIR spectral database.

In one embodiment, a gas chromatography analysis method was used to obtain the relative content of fatty acids in each rapeseed oil sample, which specifically includes 0.40 g of the rapeseed ground sample was respectively weighed in a 10 mL graduated test tube, 2 mL of petroleum ether-diethyl ether solution was added, 1 mL of 0.4 mol/L KOH—CH$_3$OH solution was added, and the mixture was uniformly mixed by vortexing, and allowed to stand and react for 2 h; the mixture was uniformly mixed by vortexing again, 2-3 mL of distilled water was added, and the mixture was allowed to stand overnight; 200 µL of an upper organic phase was taken, diluted to 1 mL with petroleum ether and subjected to analysis;

Chromatographic conditions: DB-23 column (30 m×0.25 mm×0.25 µm); the carrier gas was nitrogen at 180 mL/min and hydrogen at 30 mL/min; the air flow was 400 mL/min; the injection volume was 1 µL; the split ratio was 150:1; the gasification temperature was 250° C.; the detector temperature was 280° C.; the initial temperature of a column was 180° C., held for 2 min, programmed-heated at 3° C./min to 230° C., and held for 12 min; then the temperature was raised at 2° C./min to 224° C., and held for 0.2 min;

The relative content ($X_i$) of each fatty acid in the rapeseed sample was calculated according to the ratio of the peak areas in the gas chromatography, and the calculation formula is as follows:

$$X_i = A_i \times 100 / \Sigma A,$$

where $A_i$ was the peak area of the fatty acid i, and $\Sigma A$ was the sum of the peak areas.

A method for measuring oil content of oil cakes was used to obtain information on the oil content of each rapeseed oil sample, which specifically includes the filter paper was cut into 7.5 cm×7.5 cm size, and folded into a paper bag which was not sealed at one side, and the paper bags were numbered with a pencil and arranged in culture dishes, with no more than 20 bags per dish. The culture dishes were transferred into a 105° C.±2° C. oven together with the filter paper bags and dried for 2 h. The culture dishes were taken out, placed in a dryer and cooled to room temperature, and each bag was weighed independently (a).

The ground rapeseed sample was placed in the filter paper bags with a medicine spoon, with 1.50 g per bag, and the bags were sealed. The filter paper bags were placed in the 105° C.±2° C. oven and dried for 3 h. The filter paper bags were taken out, placed in the dryer and cooled to room temperature, and each bag was weighed independently (b).

The sample bags were loaded into a fat extractor of anhydrous diethyl ether by Soxhlet extraction such that the sample bags were completely immersed in the anhydrous diethyl ether, and the sample bags were extracted in a water bath. The temperature of the water bath was maintained at 70° C.-80° C. for extraction for 10 h. After the extraction was completed, the sample bags were taken out, the diethyl ether was volatilized in a ventilated place, and the remaining diethyl ether in the extractor was recovered. The sample bags were transferred into the 105° C.±2° C. oven and dried for 2 h. The sample bags were taken out, placed in the dryer and cooled to room temperature, and each bag was weighed separately (c). The oil content in the rapeseed sample was calculated based on mass fraction $W_i$, and the formula is as follows:

$$W_i = (b-c)/(b-a) \times 100,$$

Where, a was the mass of paper, b was the mass of paper plus the mass of the dried sample, and c was the mass of paper plus the mass of the extracted sample.

C. Establishment of a fatty acid database for rapeseeds based on gas chromatography: the relative content of linoleic acid in each sample was obtained by using the national standard method GB/T 17377-2008 *Gas Chromatography of Animal and Vegetable Fats and Oils—Analysis and Fatty Acid Methyl Esters,* and the information on oil content of each sample was obtained according to GB/T 10359-2008 *Determination of Oil Content of Oil Cakes.* The relative content of linoleic acid was converted into absolute content by using the following formulae:

$$\overline{M_i} = \sum M_j \cdot y_j,$$

$$Z = \frac{\overline{M_i}}{w_i} - 1,$$

$$y_j = x_j \cdot \frac{\overline{M_i}}{w_i},$$

where $y_j$ and $x_j$ represent the relative content (mol %) and the absolute content (mol/g) of fatty acids, respectively, $M_j$ represents the relative molecular mass of each fatty acid, $\overline{M_i}$ is the weighted average relative molecular mass of the fatty acids in the oilseed, $w_i$ represents the oil content (w/w, %), and z represents the correction coefficient for the mutual conversion of the relative content and the absolute content of fatty acids.

The relative content, absolute content and correction coefficient of linoleic acid in 510 rapeseed samples were used as effective information to form database information. The specific information is shown in Table 1.

D. Establishment of a prediction model of fatty acid in samples and prediction of fatty acid content in samples to be tested: 510 rapeseed samples were divided into a training set with 408 samples and a validation set with 102 samples in a ratio of 4:1 by K-S algorithm, and in combination with sample NIR spectra in the training set corresponding to linoleic acid in rapeseed and correction coefficient Z, competitive adaptive reweighted sampling (CARS) algorithm was used to select the corresponding important wavelength from 1,557 wavelength points. The main parameters of the variable selection model are shown in Table 2. The PLS prediction model was established by using 142 characteristic wavelengths of linoleic acid and 293 characteristic wavelengths of the correction coefficient Z in combination with the samples in the training set. The main parameters of the model are shown in Table 3. Finally, the established model was used to predict the content of linoleic acid in the samples in the validation set to calculate the predicted absolute error. In order to better highlight the effect of the present invention, the same method was used to directly predict and convert the content of linoleic acid in rapeseed. The comparison results of the predicted content and the converted content were shown in Table 4.

TABLE 1

Content of linoleic acid in rapeseed and correction coefficient range thereof.

| Chemical Value | Sample Set | Relative Content | | Absolute Content | |
|---|---|---|---|---|---|
| | | Range (mol %) | Average (mol %) | Range (mol/g) | Average (mol/g) |
| Linoleic Acid | Training Set | 11.20-20.90 | 17.00 | 1.51-3.62 | 2.55 |
| | Test Set | 11.66-20.90 | 17.51 | 1.61-3.63 | 2.67 |
| Correction Coefficient | Training Set | — | — | 4.52-7.19 | 5.65 |
| | Test Set | — | — | 4.51-6.99 | 5.63 |

TABLE 2

Variable selection model parameters of absolute content in rapeseed and correction coefficient Z of linoleic acid.

| Indicator | optPC | RMSECV | $Q^2$max | Number of Important Variables |
|---|---|---|---|---|
| Linoleic Acid | 28 | 0.08 | 0.9569 | 142 |
| Correction Coefficient Z | 45 | 0.19 | 0.9694 | 293 |

TABLE 3

PLS prediction model parameters of absolute content and correction coefficient Z of linoleic acid in rapeseed.

| Indicator | optPC | $R^2$ | RMSECV | $Q^2$max |
|---|---|---|---|---|
| Linoleic Acid | 28 | 0.9825 | 0.09 | 0.9516 |
| Correction Coefficient Z | 28 | 0.9868 | 0.16 | 0.9525 |

TABLE 4

Independent validation absolute error of PLS prediction model of linoleic acid in rapeseed.

| Indicator | Error Maximum of Absolute Content (mol/g) | Maximum Absolute Error of Relative Content | |
|---|---|---|---|
| | | Before Conversion (%) | After Conversion (%) |
| Linoleic Acid | 0.43 | 3.73 | 2.80 |

The foregoing description of the exemplary embodiments of the invention has been presented only for the purposes of illustration and description and is not intended to be exhaustive or to limit the invention to the precise forms disclosed. Many modifications and variations are possible in light of the above teaching.

While there has been shown several and alternate embodiments of the present invention, it is to be understood that certain changes can be made as would be known to one skilled in the art without departing from the underlying scope of the invention as is discussed and set forth above and below including claims and drawings. Furthermore, the embodiments described above are only intended to illustrate the principles of the present invention and are not intended to limit the scope of the invention to the disclosed elements.

What is claimed is:

1. A NIR method for fatty acid content of oilseeds, comprising the steps of:

S1: providing oilseed samples, and acquiring NIR spectra of the oilseed samples by using a near infrared spectrometer;

S2: performing standard normal transformation and second derivative data preprocessing on the acquired NIR spectra of the oilseed samples to obtain preprocessed NIR spectra, and establishing the NIR spectrum database of oilseeds;

S3: establishing a fatty acid database of oilseeds based on gas chromatography to obtain the relative content of fatty acids in each oilseed sample; using a method for measuring oil content of oilseeds to obtain information on the oil content of each oilseed sample; converting the relative content of fatty acids into absolute content; establishing the oilseed fatty acid database composed of the relative content, absolute content and correction coefficient of fatty acids as effective information;

S4: establishing a prediction model of fatty acids in oilseeds by dividing the oilseed samples into training set and validation set; using a variable selection method in combination with NIR spectra in the training set corresponding to different indicators in the fatty acid database of oilseeds to select the corresponding important wavelengths, establishing the prediction model of fatty acids in oilseeds by using the selected important wavelengths through a chemometric method combined with the absolute content and the correction coefficient of fatty acids; and validating the prediction model of fatty acids by the validation set; and S5: providing a sample for testing; acquiring the NIR spectrum of the tested sample by the infrared spectrometer; preprocessing by the preprocessing method in step S2; and importing the preprocessed NIR spectrum into the prediction model of fatty acids established in step S4 to obtain the predicted fatty acid content of the tested sample, wherein said converting the relative content of fatty acids into the absolute content in step S3 is performed according to the formulae of:

$$\overline{M_i} = \sum M_j \cdot y_j,$$

$$Z = \frac{\overline{M_i}}{w_i} - 1,$$

$$y_j = x_j \cdot \frac{\overline{M_i}}{w_i},$$

wherein $y_j$ and $x_j$ represent the relative content and the absolute content of fatty acids, respectively, $M_j$ represents the relative molecular mass of each fatty acid, $\overline{M_i}$ is the average relative molecular mass of the fatty acids in the oilseeds, $w_i$ represents the oil content, and z represents the correction coefficient for the mutual conversion of the relative content and the absolute content of fatty acids.

2. The method of claim 1, wherein each oilseed sample is repeatedly measured 3-9 times in step S1.

3. The method of claim 1, wherein the collection conditions of NIR spectra in step S1 are the collection temperature of the oilseed sample being 20±5° C., the NIR spectrum measurement range being 4,000-10,000 cm$^{-1}$, the number of scans being 64, and the measurement method being reflection.

4. The method of claim 1, wherein the chemometric method in step S4 comprises variable selection methods including Competitive Adaptive Reweighted Sampling (CARS-PLS), Orthogonal Projection to Latent Structures (OPLS) variable combination population analysis (VCPA), and the modeling method comprises partial least squares, multiple linear regression and BP-neural network modeling methods.

* * * * *